US012570941B2

(12) United States Patent
Perozziello et al.

(10) Patent No.:  US 12,570,941 B2
(45) Date of Patent:      Mar. 10, 2026

(54) MICROFLUIDIC DEVICE FOR CELL CULTURE AND SCREENING AND RELATED PRODUCTION METHOD

(71) Applicants: UNIVERSITA' DEGLI STUDI MAGNA GRAECIA DI CATANZARO, Catanzaro (IT); UNIVERSITY OF BERN, Bern (CH)

(72) Inventors: Gerardo Perozziello, Borgia (IT); Francesco Guzzi, Cotronei (IT); Elvira Parrotta, Catanzaro (IT); Giovanni Cuda, Catanzaro (IT); Maria Laura Coluccio, Borgia (IT); Patrizio Candeloro, Crotone (IT); Gina Valentino, Bern (CH); Paola Luciani, Bern (CH)

(73) Assignees: UNIVERSITA' DEGLI STUDI MAGNA GRAECIA DI CATANZARO, Catanzaro (IT); UNIVERSITY OF BERN, Bern (CH)

( * ) Notice: Subject to any disclaimer, the term of this patent is extended or adjusted under 35 U.S.C. 154(b) by 586 days.

(21) Appl. No.: 18/002,099

(22) PCT Filed: Jun. 17, 2021

(86) PCT No.: PCT/IB2021/055369
§ 371 (c)(1),
(2) Date: Dec. 16, 2022

(87) PCT Pub. No.: WO2021/255687
PCT Pub. Date: Dec. 23, 2021

(65) Prior Publication Data
US 2023/0235260 A1     Jul. 27, 2023

(30) Foreign Application Priority Data
Jun. 19, 2020    (IT) ........................ 102020000014815

(51) Int. Cl.
| | |
|---|---|
| *C12M 3/06* | (2006.01) |
| *B01L 3/00* | (2006.01) |
| *C12M 1/00* | (2006.01) |

(52) U.S. Cl.
CPC ....... *C12M 23/16* (2013.01); *B01L 3/502707* (2013.01); *B01L 3/502715* (2013.01);
(Continued)

(58) Field of Classification Search
None
See application file for complete search history.

(56) References Cited

U.S. PATENT DOCUMENTS

| | | | |
|---|---|---|---|
| 8,372,358 B2 * | 2/2013 | Groisman | .............. C12M 41/36 |
| | | | 422/68.1 |
| 2006/0166357 A1 * | 7/2006 | Takayama | ......... B01L 3/502738 |
| | | | 435/289.1 |

(Continued)

FOREIGN PATENT DOCUMENTS

| | | |
|---|---|---|
| CN | 105670929 A | 6/2016 |
| WO | 2012/033439 A1 | 3/2012 |

(Continued)

OTHER PUBLICATIONS

International Search Report and Written Opinion issued on Sep. 20, 2021, in corresponding International Application No. PCT/IB2021/055369, 11 pages.

*Primary Examiner* — Brian R Gordon
(74) *Attorney, Agent, or Firm* — Maier & Maier, PLLC

(57)          ABSTRACT

A microfluidic device for cell culture and screening includes a covering element, an intermediate element, and a lower element. The intermediate element has a plurality of microchannels, a plurality of supply tanks, and at least one waste tank. The intermediate element is positioned between the covering element and the lower element to define an upper optical window and a culture chamber. The plurality of (Continued)

microchannels fluidly connect supply tanks, culture chamber, and waste tank, enabling passive and controlled fluid flow.

11 Claims, 8 Drawing Sheets

(52) U.S. Cl.
CPC .......... *C12M 23/40* (2013.01); *B01L 2200/16* (2013.01); *B01L 2300/0883* (2013.01); *B01L 2300/0887* (2013.01); *B01L 2300/168* (2013.01)

(56) References Cited

U.S. PATENT DOCUMENTS

| | | | | |
|---|---|---|---|---|
| 2010/0291588 | A1* | 11/2010 | McDevitt | G01N 33/491 |
| | | | | 435/287.1 |
| 2011/0044865 | A1 | 2/2011 | Groisman et al. | |
| 2011/0182775 | A1* | 7/2011 | Kitamura | B29C 66/53461 |
| | | | | 422/68.1 |
| 2012/0184010 | A1* | 7/2012 | Medoro | B03C 5/026 |
| | | | | 435/173.9 |
| 2012/0190128 | A1* | 7/2012 | Nikbakht | B01F 33/30 |
| | | | | 422/68.1 |
| 2016/0375438 | A1* | 12/2016 | Marcy | B01L 9/527 |
| | | | | 506/39 |
| 2017/0002315 | A1* | 1/2017 | Urisu | C12M 25/06 |
| 2017/0016060 | A1* | 1/2017 | Sabounchi | B01L 3/5027 |
| 2017/0191956 | A1* | 7/2017 | Kuwabara | B01L 3/502707 |
| 2017/0241878 | A1* | 8/2017 | Broyer | G01N 1/4077 |
| 2017/0252740 | A1* | 9/2017 | Okada | B01L 3/50273 |
| 2018/0015464 | A1* | 1/2018 | Levner | B01L 3/502746 |
| 2018/0272346 | A1* | 9/2018 | Griffith | C12M 25/04 |
| 2018/0369813 | A1* | 12/2018 | Delamarche | F16K 99/0034 |
| 2020/0071727 | A1* | 3/2020 | Tandon | C12M 35/02 |
| 2020/0086312 | A1* | 3/2020 | Hiddessen | B01L 3/50273 |
| 2020/0164368 | A1* | 5/2020 | Zagnoni | B01L 3/502761 |
| 2021/0031186 | A1* | 2/2021 | Eberwine | B01L 3/00 |
| 2021/0245156 | A1* | 8/2021 | Lin | C12M 47/04 |
| 2022/0106547 | A1* | 4/2022 | Petropolis | C12N 5/0688 |
| 2022/0204903 | A1* | 6/2022 | Nordon | C12M 29/10 |
| 2022/0275434 | A1* | 9/2022 | Mikkelsen | B01L 3/502761 |
| 2023/0235260 | A1* | 7/2023 | Perozziello | B01L 3/502715 |
| | | | | 435/305.2 |
| 2024/0010962 | A1* | 1/2024 | Singh | C12M 35/04 |
| 2025/0231389 | A1* | 7/2025 | Kawai | C12M 1/34 |
| 2025/0236829 | A1* | 7/2025 | Nordon | C12M 23/24 |

FOREIGN PATENT DOCUMENTS

| | | | |
|---|---|---|---|
| WO | 2013/082612 | A1 | 6/2013 |
| WO | 2019/157170 | A1 | 8/2019 |
| WO | 2020/028974 | A1 | 2/2020 |

* cited by examiner

MICROFLUIDIC DEVICE FOR CELL CULTURE AND SCREENING AND RELATED PRODUCTION METHOD

FIELD

The present invention relates to the technical field of microfluidic devices for cell cultures and screening. In particular, the present invention relates to a microfluidic device that can be used to carry out cultures, reprogramming, expansions and differentiation, cell monitoring. The microfluidic device according to the invention finds application in monitoring the effects of drugs on cell populations in the pharmaceutical and medical fields, reprogramming, expansion and differentiation of stem cells in tissue and medical engineering.

The present invention also relates to a production method of the microfluidic device.

BACKGROUND

As is known, microfluidic systems allow excellent control of the microenvironment, which is useful for performing high-throughput cell screening. Some publications of studies relating to passive devices are known, however the microfluidic devices currently in use require external interventions or active energy sources in order to function. Most of the currently known microfluidic systems are provided with external pressure sources which ensure constant flow rates, ie they are active in character, cannot be defined as passive devices and are substantially closed devices.

Although in the configurations of currently known microfluidic devices, the regulation of the flow rate is simple and versatile, these devices require specialized personnel who know how to operate them, an external power supply many components which are more complex.

Furthermore, currently known closed systems limit the accesses to the various culture compartments.

SUMMARY

The purpose of the present invention is to provide a microfluidic device for cell cultures and screening that is passive, i.e. does not require external interventions or active energy sources in order to function.

Furthermore, the purpose of the present invention is to provide a microfluidic device that allows access to treated cell samples for their easy recovery and subsequent analysis using conventional tools and equipment.

Finally, the purpose of the present invention is to provide a microfuidic device capable of operating inside conventional incubators or dedicated mini-incubators coupled to conventional optical instruments.

According to the present invention, a microfluidic device for cell cultures and screening is realized.

BRIEF DESCRIPTION OF THE DRAWINGS

For a better understanding of the present invention, a preferred embodiment is now described, purely by way of non-limiting example, with reference to the attached drawings, in which.

DETAILED DESCRIPTION

Figure 1:
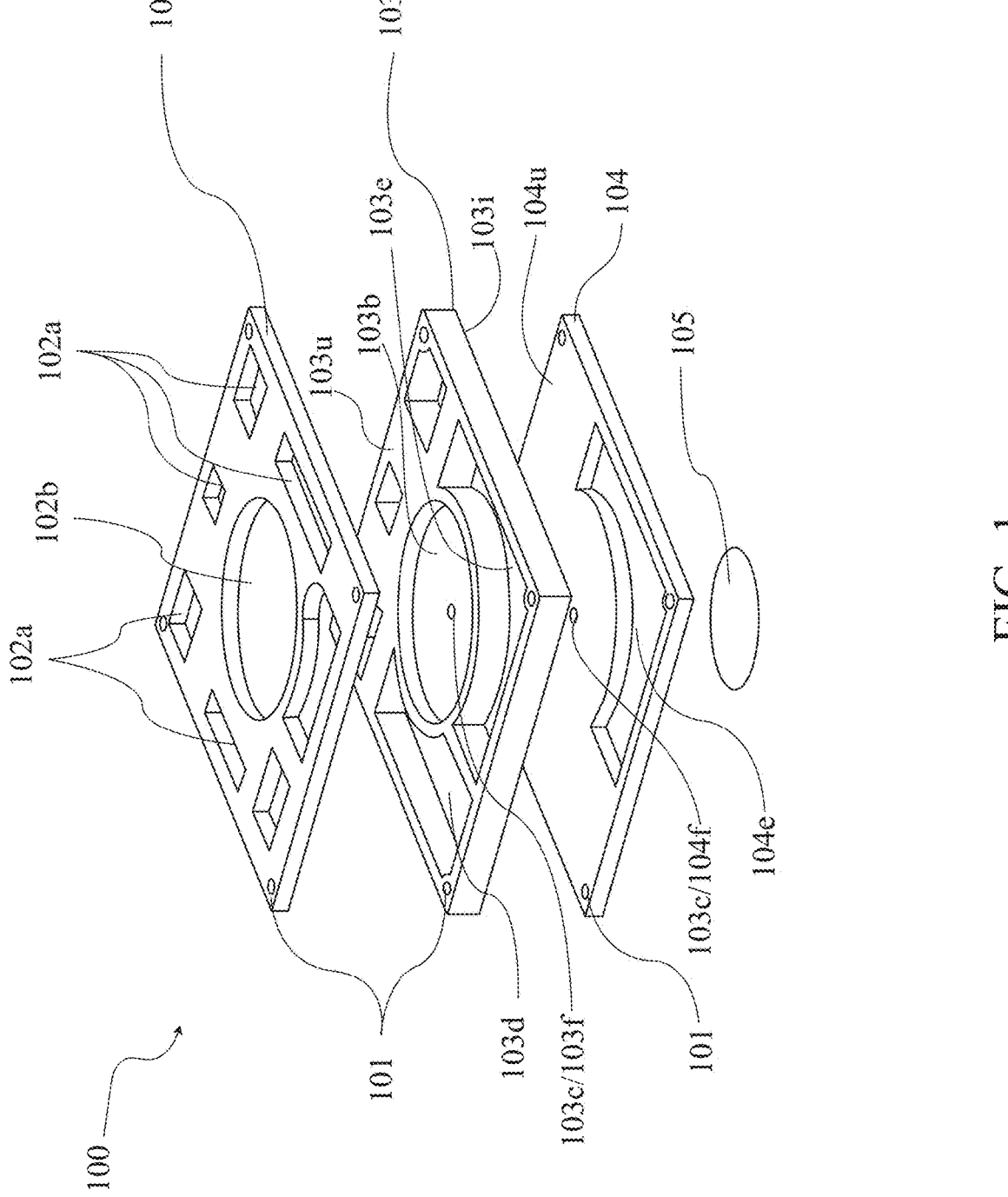
FIG. 1 shows an exploded view of the microfluidic device, according to the invention.

With reference to the figures and in particular to FIG. 1, the microfluidic device 100 for cell cultures and screening according to the invention comprises a chip consisting of a plurality of layers, in particular of a covering element 102, an intermediate element 103 and an element bottom of PMMA, and a slide 105.

According to an aspect of the invention the slide 105 can be made of CaF2, or of quartz, or other types of glass such as borosilicates, aluminosilicates, soda lime, or of some types of polymer (PMMA, PC, COC, PS, . . . ), namely of all those types of materials that are optically transparent.

Each element 102, 103, 104 has at least four alignment holes 101, located at the ends of each side, and preferably having a diameter of 3 mm. These alignment holes 101 are adapted to allow the assembly step of the microfluidic device 100.

As shown in FIG. 1, the chip consists of a plurality of layers consisting of:

a cover element 102 in PMMA;

an intermediate element 103 equipped with microchannels 103a;

a lower element 104, and a slide 105.

The covering element 102 consists of a first layer of PMMA with a substantially flat shape having a thickness between 5 mm and 1 mm, preferably equal to 3 mm, worked on both its faces. A first internal face of the covering element 102 has a plurality of openings 102a that allow the insertion of fluids inside the supply tank 103d and waste tank 103e, formed in the intermediate underlying layer, and their subsequent withdrawal. Said openings 102a are advantageously made so that the area near the microchannels 103a is accessible, so as to facilitate the injection and aspiration of liquids. An external face of the covering element 102 has a through h hole 102b with a diameter preferably of 39 mm, which constitutes an upper optical window 106 which is formed following the assembly of the microfluidic device 100.

The intermediate element 103 equipped with channels consists of a second layer of PMMA with a thickness, between 4 mm and 8 mm, preferably equal to 6 mm and worked on both its faces. A lower face 103i of the intermediate element 103 comprises a plurality of microchannels 103a, preferably five microchannels 103a, which constitute an extensive microfluidic network in which each microchannel 103a preferably measures a length equal to 300 mm and having a rectangular section having a width between 0.005 mm and 0.5 mm, preferably equal to 0.254 mm, and a height between 0.005 mm and 0.5 mm, preferably equal to 0.100 mm.

The lower face 103i comprises at least one culture chamber 103c, a plurality of supply tanks 103d, preferably four, and at least one waste tank 103e connected to each other by means of the microchannels 103a. The supply tanks 103d and the waste tank 103e are accessible from the outside through the openings 102a in such a way as to be able to enter and remove the fluids that the tanks contain in use.

An upper face 103u of the intermediate element 103 comprises a blind bottom cavity 103b, which, upon assembly with the covering element 102, constitutes a portion of the upper optical window 106. The blind bottom cavity 103b has a diameter corresponding to the through hole 102b and preferably equal to 39 mm, and is lowered by 3 mm with respect to the upper surface of the intermediate element 103.

The lower element 104 consists of a third layer of polymethylmethacrylate (PMMA) having a thickness between 5 mm and 1 mm, preferably equal to 3 mm, worked on both its faces, a lower face and an upper face.

The upper face 104u of the lower element 104 is in use facing the interior of the microfluidic device 100 to close the microchannels 103a. The upper face 104u includes a collection tank 104e defined as a lowered portion, or a cavity with a blind bottom, preferably 2.7 mm deep and at a lower level than the final height to which the outlet channel opens. In addition, the upper face includes a central through hole 104f for the culture chamber 103c.

The lower face 1041 of the lower element 104 comprises a recessed central re-entrant portion 107, preferably of 2.20 mm, which constitutes the lower central optical window following assembly of the device 100. The re-entering recessed central portion 107 has a diameter corresponding to the through hole 102b and to the cavity a blind bottom 103b, preferably equal to 39 mm.

Figure 2:
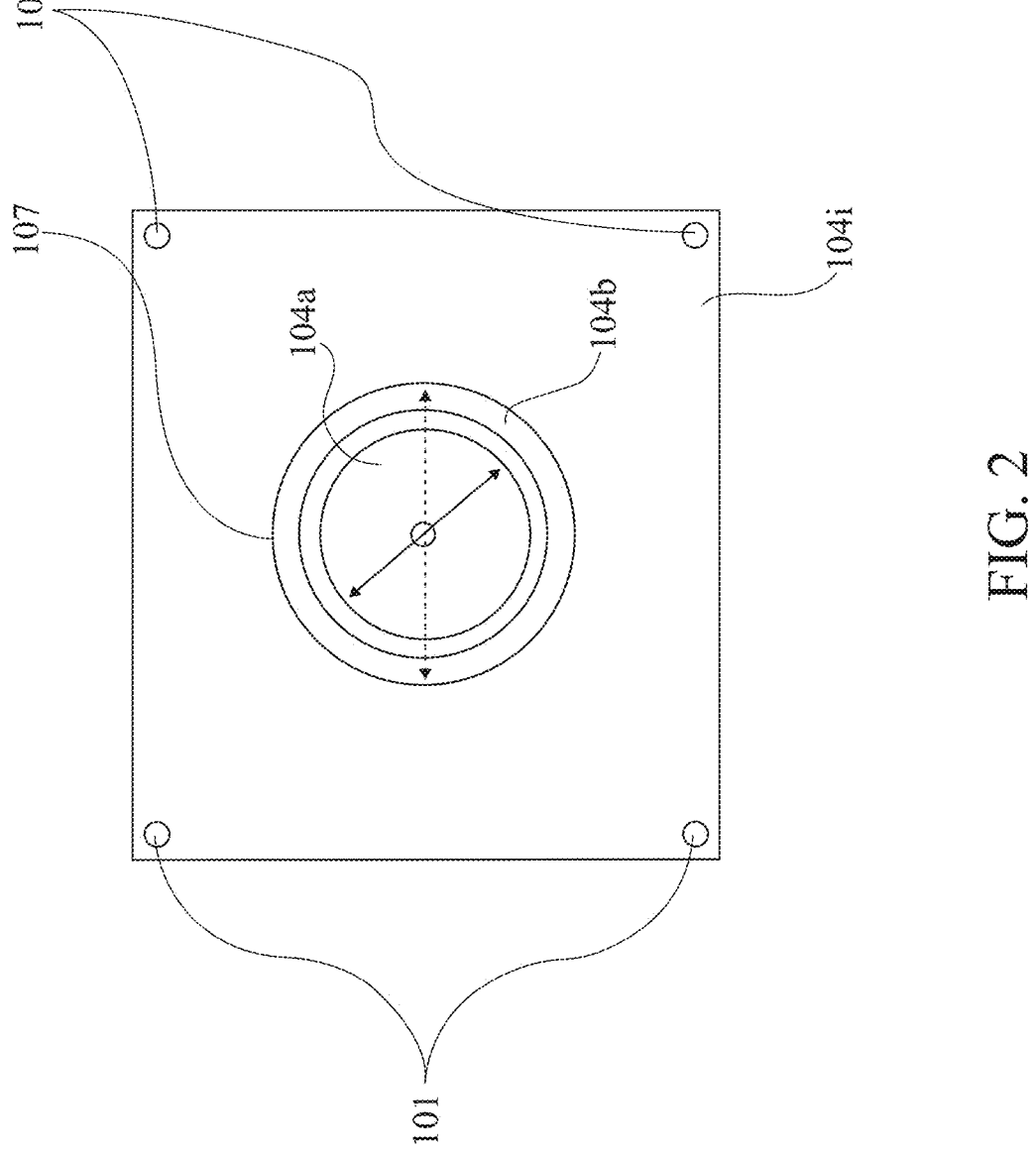
FIG. 2 shows a schematic view from below of a portion of the microfluidic device, according to the invention.
Figure 3:
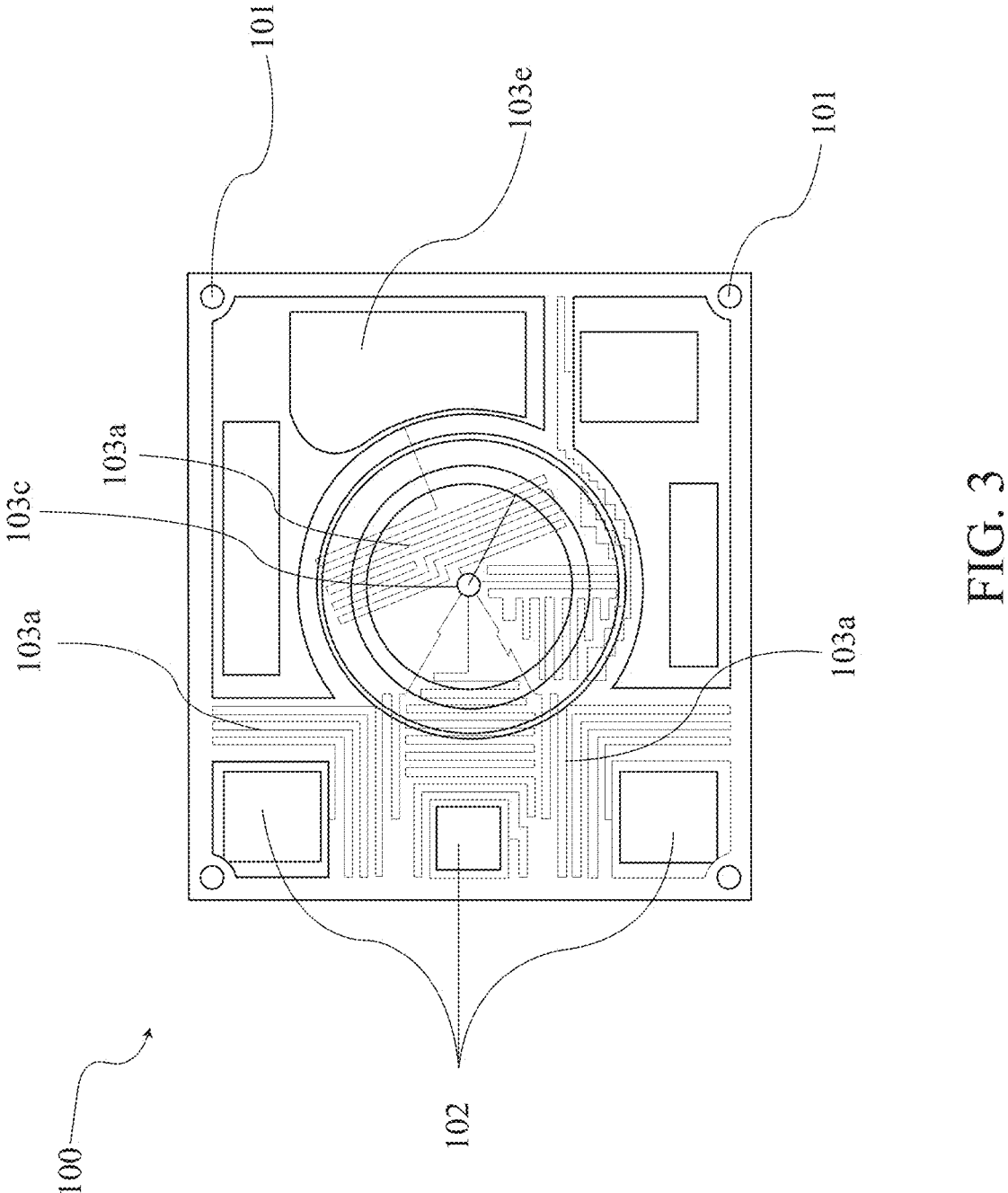
FIG. 3 is a top view of the assembled microfluidic device, according to the invention.
Figure 5:
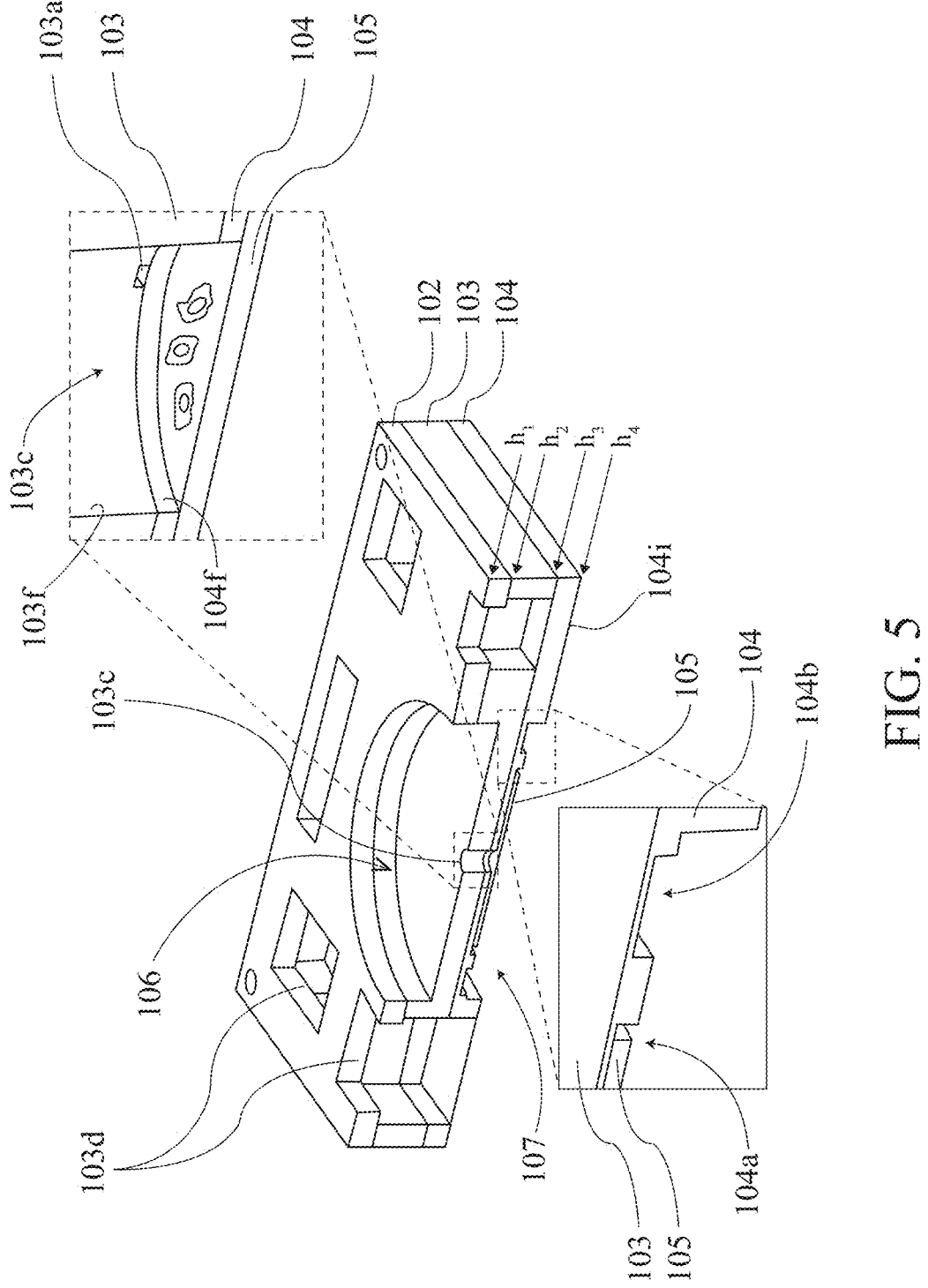
FIG. 5 shows a sectional view of the microfluidic device, according to the invention.

Inside the incoming recessed central portion 107, or lower optical window, there is a housing pocket 104a for housing the slide 105, preferably having a diameter of 26 mm and a depth of 0.600 mm. As shown in FIGS. 2 and 5, the lower face also comprises a second circular pocket 104b with a stepped profile having an external diameter preferably equal to 37.50 mm and an internal diameter preferably equal to 30.5 mm, recessed with respect to the lower surface of the element 104, of 0.600 mm, made for the hollow cylindrical support used inside a mini-incubator in the experimental phase and placed between the housing pocket of the slide 105 and the portions of element 104 that define the lower optical window 107.

The intermediate element 103 in use, and following assembly, is fixed between the covering element 102 and the lower element 104, resulting interposed between them, forming the upper optical window 106 in a central position. According to a preferred embodiment, the cover element 102, the intermediate element 103 and the lower element 104 have sides with dimensions of 80 mm×72 mm.

As shown in the detail view of FIG. 5, the culture chamber 103c consists of a central through hole 103f obtained in the intermediate layer 103 and a central through hole 104f obtained in the upper face of the lower layer 104, and closed at the bottom by the slide 105.

The slide 105 is able to be housed in the housing pocket obtained in the lower element 104. The slide 105 preferably has a diameter of 25 mm and a thickness of between 0.2 mm and 0.9 mm, preferably equal to 0.5 mm. The slide 105 closes the central culture chamber 103c at the bottom as shown in FIG. 5.

In use, cells adhere on the slide 105, during culturing. Consequently, in use, the cells are located at a distance of 3.2 mm from the beginning of the upper optical window 106 and 0.200 mm below the microchannels 103a.

Advantageously, in use, the microfluidic device 100 is totally passive. Thanks to the specific geometry of device 100, the difference in fluid levels between reservoirs 103d and culture chamber 103c generates a pressure gradient. This gradient allows the movement of the fluid inside the microchannels 103a ensuring a certain flow rate, in accordance with their calculable hydraulic resistance, in the case of a quadrangular section channel, with the following formula:

$$R = \frac{12\eta L}{wh^3} = \frac{12 \cdot (0.001001 \text{ Pa} \cdot \text{s}) \cdot 300 \text{ mm}}{0.254 \text{ mm} \cdot (0.100 \text{ mm})^3} = 14187.40 \frac{\text{Pa} \cdot \text{s}}{\text{mm}^3} \quad (1)$$

where $\eta$ is the viscosity of the water.

The height of the fluid influences the flow rate, it is therefore important that the tanks 103d have a sufficiently large surface to allow a slow decrease of the liquid level inside.

Figure 4:
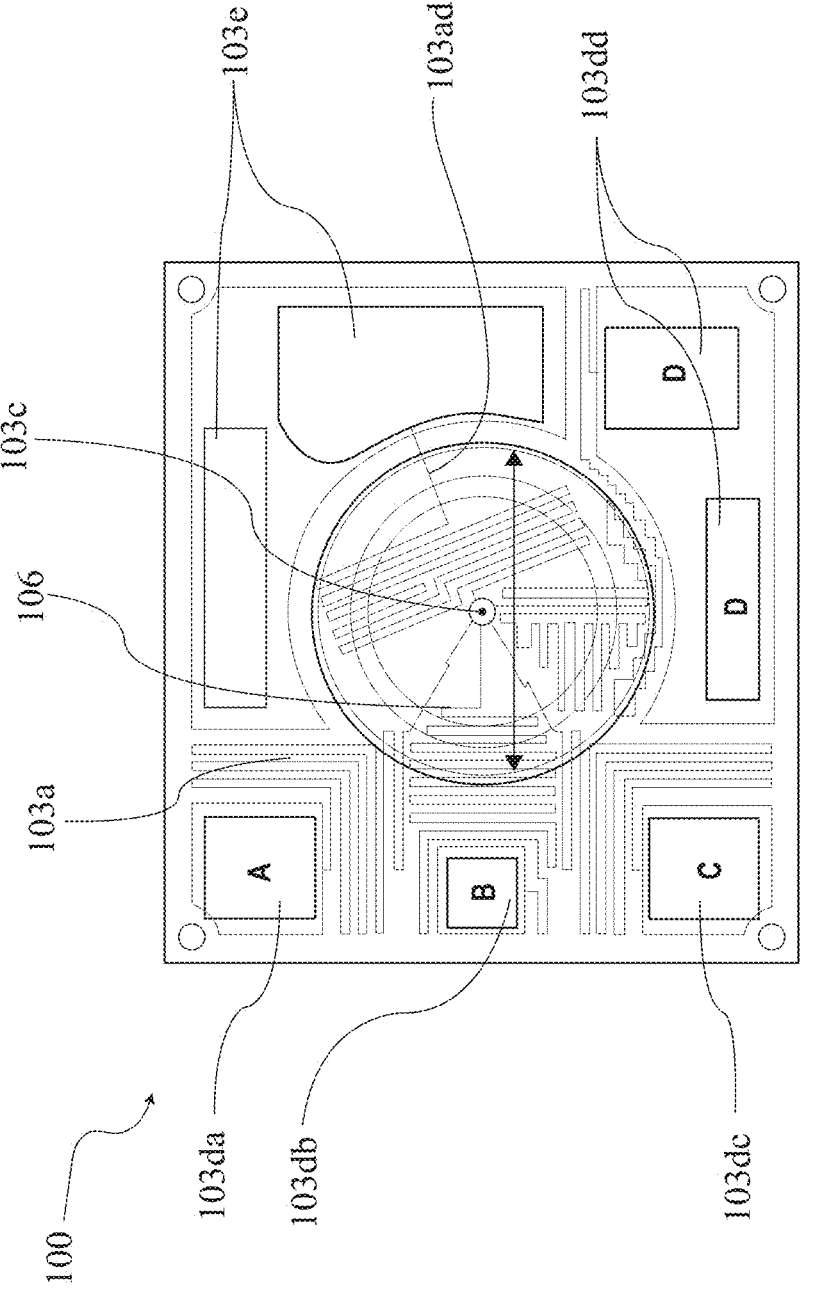
FIG. 4 shows a second top view of the microfluidic device, according to the invention.

With reference to FIG. 4, the microfluidic device 100 comprises four supply tanks 103d each having a volume such as to provide a sufficient flow rate in the microchannels for a time ranging from 12 hours to 1440 hours. A first tank 103da and a third tank 103dc have characteristics such as to allow an acceptable flow rate for 48 hours. A second tank 103cb can be used to have a sufficient flow rate for 24 hours, while a fourth tank 103dd has characteristics and dimensions such as to allow an acceptable flow rate for 168 hours or for 7 days. In particular, preferably, the first tank 103da has a volume of 10307.58 μl, the second tank 103db has a volume of 600 μl, the third tank 103dc has a volume of 1307.58 μl while the fourth tank 103dd has a volume of 4681.5 μl.

Each supply tank 103da, 103db, 103dc, 103dd must be used excluding the other tanks by closing the tanks that are not needed during the specific use.

The microfluidic device 100 is advantageously sized so as to have hydraulic resistances of all the inlet microchannels equal to that of the discharge microchannel 103ad towards the waste tank 103e. It is therefore necessary for fluid dynamics reasons that only one tank at a time can be in operation.

Each channel entering or leaving the culture chamber is located at a height between 0.005 mm and 0.5 mm from the bottom of the chamber itself, to which the cells adhere in use. This conformation advantageously allows cell proliferation minimally affected by the shear stresses caused by the flows of liquid flowing in the channels. In each channel, the flow rate of fluid Q that can be calculated with the Hagen-Poiseulle equation is equal to:

$$Q = \frac{\Delta P}{R} = \frac{\rho g \Delta H}{R} \rightarrow \qquad (2)$$

$$\rightarrow \frac{0.001 \left(\frac{\text{g}}{\text{mm}^3}\right) \cdot 9822 \left(\frac{\text{mm}}{\text{s}^2}\right) \cdot (6 \text{ mm} - 2 \text{ mm})}{14187.40 \frac{\text{Pa} \cdot \text{s}}{\text{mm}^3}}$$

$$\rightarrow \rightarrow 0.002769 \left(\frac{\mu l}{\text{s}}\right) \approx 9.969 \left(\frac{\mu l}{\text{h}}\right)$$

Where $\rho$ is the density of the water and $\Delta H$ is the difference in height between the fluid columns of the tank (equal to 6 mm when it is completely full) and in the culture chamber above the microchannel (2 mm). The pressure is a function of the difference between the columns of fluid according to Stevino's law.

The plurality of reservoirs having different characteristics allows the device 100, advantageously, to implement protocols of expansion, and/or differentiation and/or reprogramming of stem cells for tissue engineering purposes or to subject the cell sample to different drugs at different times in the pharmaceutical or personalized medicine field. In these uses there is in fact the need to dispense different reagents at different instants of time in the central culture chamber.

From the at least one culture chamber 103c the discharge microchannel 103ad departs and flows into the waste tank 103e, consisting of a lowered and deep pocket 2.7 mm made on the internal face of the lower element 104 of the device 100. Advantageously, the lowered pocket maintains the pressure on the channel in the outlet tank as insignificant as possible. In fact, until the fluid level in the waste tank 103e has reached the height of the microchannel, we will have a zero outlet pressure ensuring a maximization of the outflow from the culture chamber.

Advantageously, the optical windows obtained above and below the device 100 allow the objectives of optical instruments (for example microscopes) in direct and inverted configuration to get as close as possible to the samples present in the culture chamber to carry out microscopic and/or microscopic or spectroscopic investigations.

According to an aspect of the invention, the microfluidic device 100 comprises a plurality of valves 108, passive or active, such as to manage flows inside the various microchannels, or water-soluble materials can be used which temporarily obstruct the microchannels and which solubilize over a specified period of time. Obviously, the management of the flows can also be carried out by acting at the level of the various hydrodynamic resistances. In addition, it is also possible to put in parallel a plurality of culture chambers supplied or not by the same tanks as shown in FIG. 6.

Figure 6B:
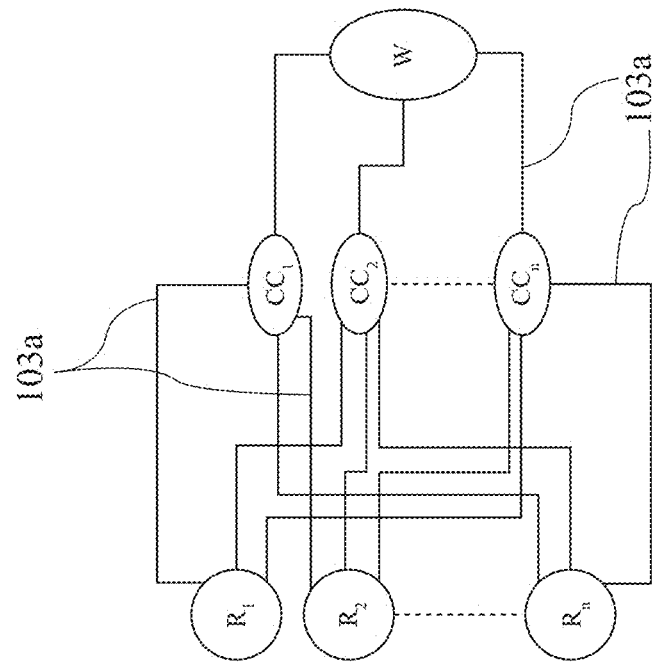
FIG. 6b shows a scheme of microfluidic networks of the microfluidic device with a plurality of culture chambers in parallel, according to the invention.
Figure 6A:
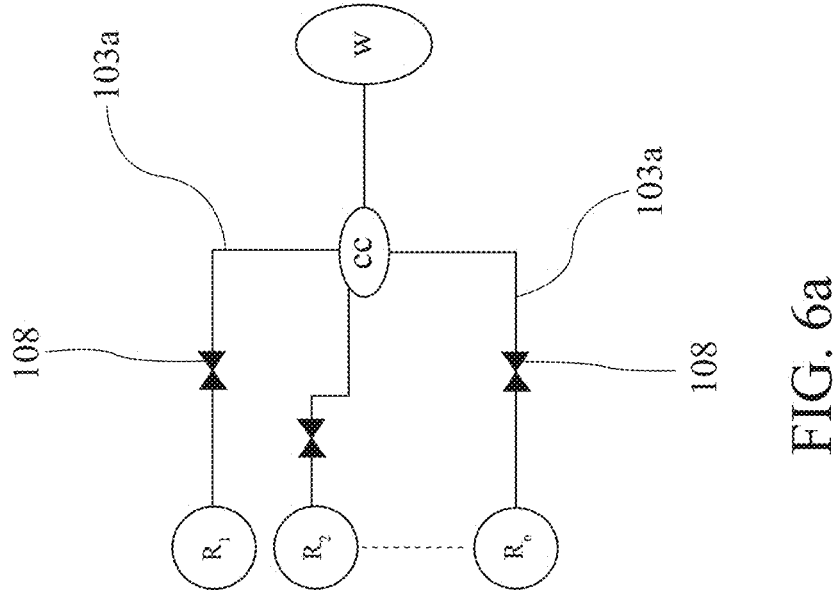
FIG. 6a shows a scheme of microfluidic networks of the microfluidic device with a plurality of tanks connected to a single culture chamber, according to the invention.

In particular, FIG. 6a shows a microfluidic network that connects a plurality of reservoirs (R1, R2, . . . . Rn) with a single culture chamber (CC). The drainage channel departs from the culture chamber towards the drainage tank (indicated by W in FIG. 6a). The flows inside the microchannels are regulated by means of active or passive 108 valves placed along the microchannels themselves.

FIG. 6b instead shows a microfluidic network having a plurality of culture chambers (CC) placed in parallel, and a plurality of tanks (R1, R2, . . . . Rn) which supply all the culture chambers. From each culture chamber a micro drainage channel departs towards the drain tank (W).

The Applicant has carried out experimental tests to support the optimal functionality of the microfluidic device 100.

The microfluidic device 100, following sterilization in an autoclave, is used to carry out cell cultures. HeLa cells were cultured for 72 hours, observing a cell growth trend comparable to what is present in the literature. The optimization of the volumes of the tanks and of the geometries is possible to carry out the experiment without carrying out a new filling of the tanks for the entire duration of the crop. At the end of the culture, a perfect adhesion of the cells to the slide 105 is appreciated without they have been disturbed by the flow rates of fluid present in the microfluidic device 100. If the flow rates of fluid were too high, the cells could be moved from the culture chamber. Furthermore, there is a noticeable increase in the number of cells upon reaching confluence. At the end of the culture, the microfluidic device 100 can be placed under an optical instrument (for example a micro-scope) or a spectroscopy instrument (for example Raman) to carry out cellular screening and investigate the biochemical constituents. By selecting a region of interest, a Raman map of the entire area is acquired. Following processing steps to which the spectra obtained are subjected, a plot of the PC3 loadings is obtained.

Figure 7:
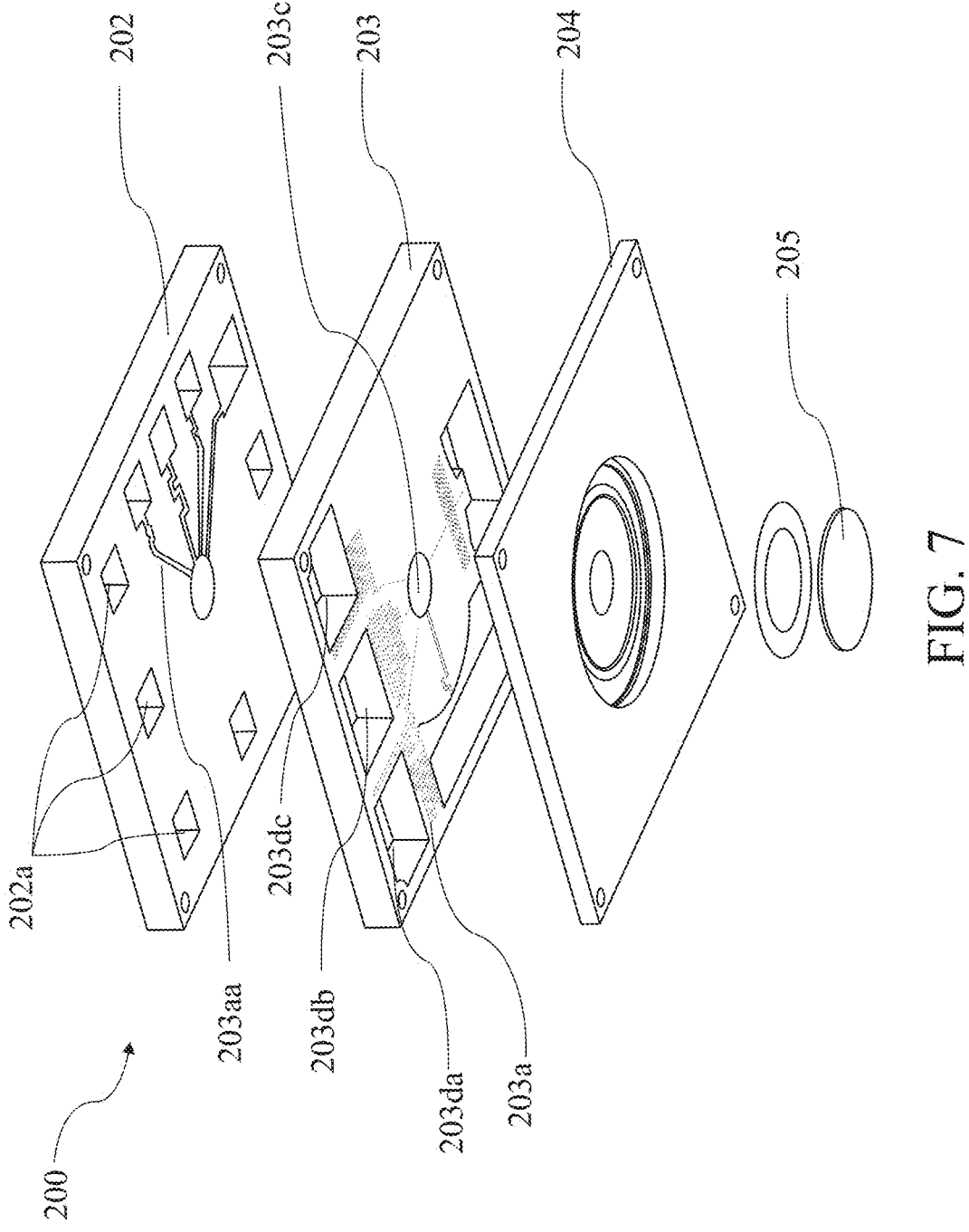
FIG. 7 shows an exploded view of a second embodiment of the microfluidic device, according to the invention.

According to a second embodiment of the invention, the device 200 is shown in FIG. 7. The device 200 comprises a mechanism for managing cascade microchannels 203aa which are located on the covering element 202, namely at a different level than that of the culture microfluidic circuit located in the intermediate element 203.

Advantageously according to the invention, a plurality of microchannels can be realized on different levels and make more use of the device area. Furthermore, these microchannels do not perturb the device functioning if each of them is coupled to a respective output microchannel of equal resistance. This allows to have several microchannels in parallel interacting with the central culture chamber 203c without disturbing the circuit. The cascade microchannels can be made with dimensions of width and depth ranging from hundreds of micrometers to a few millimeters, while the third dimension can vary from hundreds of micrometers to hundreds of mm.

In this specific case, the four different inlet cascade microchannels 203aa cool the medium inside the culture chamber one at a time, which will be disposed of through the outlet cascade microchannel 203a located in the intermediate layer 203. The main microfluidic network is not disturbed by the presence of the cascaded channels 203aa if these are coupled to output channels 203a of the same flow rate. A double-sided tape is used for the gluing process of the slide 205.

On hydrophilic substrates, even with small flow rates, flows towards the culture chamber 203c can be obtained.

In the case of poorly wettable substrates, however, the presence of a concave meniscus in the microchannels will make it difficult for the fluid to spontaneously escape, making it necessary to use higher pressures capable of overcoming the hydrophobic forces and this is reflected in the height of the liquids introduced into the wells connected to the channels. In hydrophobic substrates, a treatment with hydrophilic substances (eg PEG) could improve the situation.

Flow to the central culture chamber 203c is ensured by the difference in height between the fluid level in the feed tank and that in the culture chamber. In particular, it should be noted how the outlet pressure on the inlet cascade microchannel 203aa is zero since the microchannel is built on a layer higher than that where the culture chamber and the main microfluidic network lie. By doing so, the microchannel does not disturb the system since it is coupled to a microchannel of equal resistance towards the cascade waste.

According to an aspect of the invention, the cascade microchannels 203aa have two dimensions (width and depth) in the order of tenths of mm or mm, while the third dimension is in the order of tens of mm.

Figure 8:
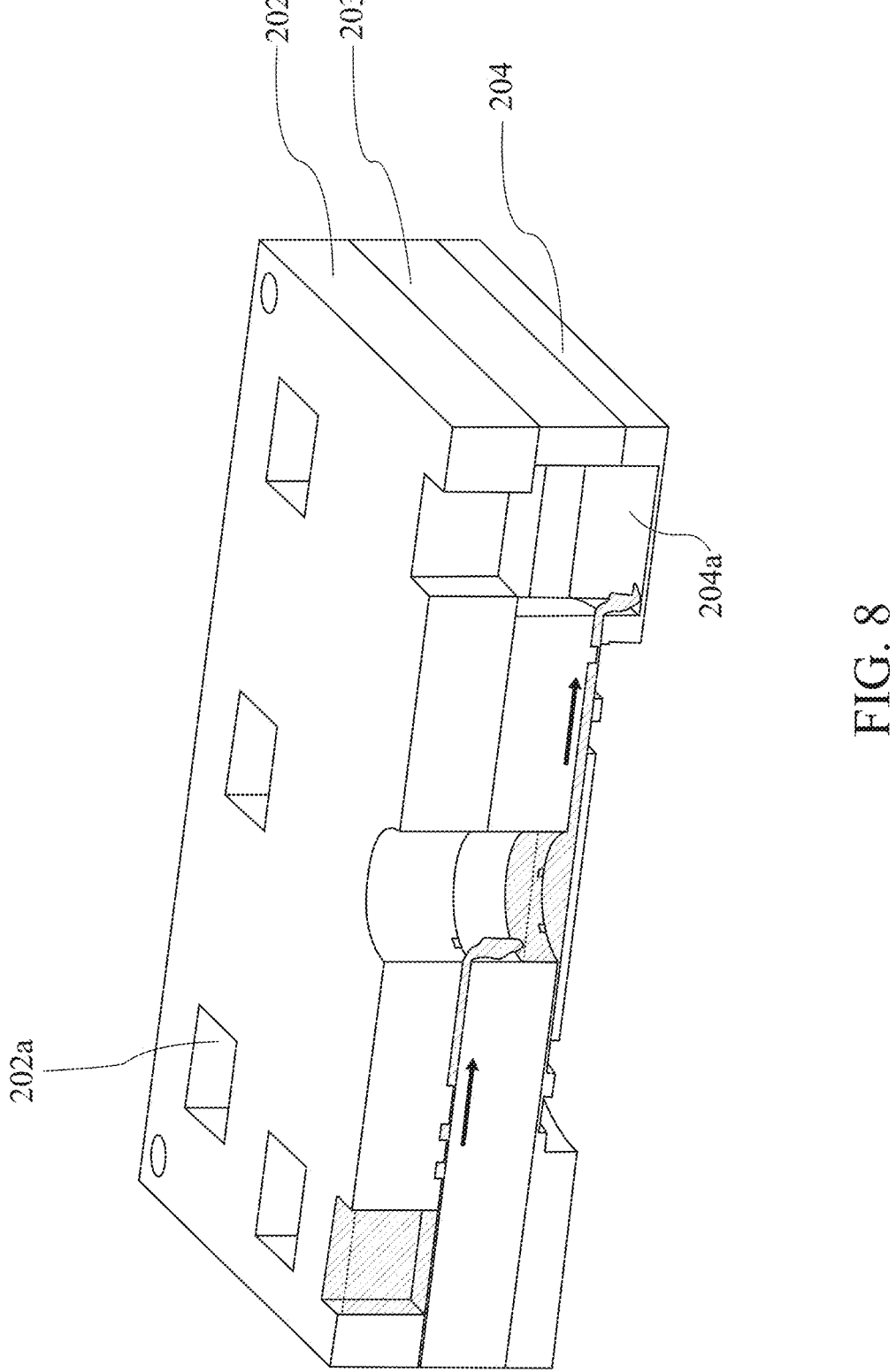
FIG. 8 shows a sectional view of the second embodiment of the microfluidic device, according to the invention.

Their geometric dimensions concur in determining a low fluid dynamic resistance, which results in very rapid flow rates capable of refreshing the reagents in the culture chamber 203c in a time ranging from a few seconds to a few minutes, depending on of the sizing adopted. Obviously, care must be taken not to affect cell adhesion with excessively high flow rates. In this specific case, the flow rates used range from a few units to of tens microliters per second. In order to guarantee an adequate flow rate, these microchannels must be fed by tanks containing columns of fluid high enough, in order to maximize the pressure at the base of the tank. To do this, it is advisable to try to make tanks large enough to minimize as much as possible the decrease in volume and, consequently, in height according to the following relationship:

$$\Delta V = A \Delta A \qquad (4)$$

where $\Delta V$ represents the volume variation contained in the tank, given by the product between the base surface A and the height variation $\Delta H$. In fact, a greater height will result in a greater pressure at the base of each and every well. To maximize the pressure difference between the inlet and outlet of the microchannel in cascade, the pressure at its outlet must be kept as low as possible, possibly zero. To do this, it will be necessary to size one or more microchannels of outflow from the culture chamber 203c to a second waste reservoir 204a, shown in FIG. 8, with an overall flow rate equal to that of the inlet of the cascade flows to the culture chamber 203c. In this way, the height of the fluid levels inside the culture chamber 203c will be kept constant at a predetermined level, not going to get wet and, consequently, creating pressure on the outlet of the inflow microchannel. The second waste reservoir is always created by means of a lowered pocket in the lower layer 204 of the microfluidic device 200. Switching the various microchannels and waste reservoirs can take place through the use of caps, passive or active valves or by means of water-soluble materials.

The present invention also relates to a method for production of a microfluidic device 100 for cell culture and screening, according to claim 10.

The manufacturing method of the microfluidic device 100 comprises the steps of:

making the upper element 102, the intermediate element 103 and the lower element 104 by means of micro-milling.

The plurality of PMMA layers, i.e. the upper element 102, the intermediate element 103 and the lower element are made using the micro-milling technique and finished by hand to optimize alignment and adhesion to each other during the subsequent alignment and assembly. The elements are then cleaned by ultrasonic cavitation in a bath of distilled water and assembled by means of solvent-assisted bonding.

In the solvent-assisted bonding phase, the elements 102, 103, 104 or the layers of PMMA are placed in a very large beaker filled with ethanol, so as not to be in contact with each other and avoid involuntary adhesion, and are completely submerged in the solvent. The beaker, or container, is covered with aluminum foil to prevent the ethanol from evaporating. After a time interval t1 preferably equal to 80 minutes, the layers are removed from the container and from the ethanol and rapidly assembled and immobilized in their final mutual position, superimposed on each other and fixed by means of a plurality of screws placed in the holes of alignment. The system composed of the three superimposed elements 102, 103, 104 is then placed in a pneumatic press preheated on both contact faces at 45° C. and a force of 1.5 kN is applied for a time t2 preferably equal to 70 min.

At the end of the bonding phase, a control phase of the device is carried out, verifying that the parts of interest are correctly welded.

The upper and lower optical windows are then made. For each of the optical windows, the assembled device is fixed on the working surface of a micro-mill and the tool tip is aligned with respect to the device along the three dimensions. The device is worked on both faces, making the upper optical window 106 on the upper face, while on the lower face a lower optical window 107 and the housing pocket 105a for the slide 105 are made. Then the slide 105 is glued into the pocket housing by depositing PMMA A3, or alternatively A20 depending on the desired viscosity, on the edges of the slide 105 and on its surface, avoiding to let the polymer go into the culture chamber area to avoid the risk of occlusion of the microchannels.

The device is then placed in a preheated oven at 70° C. for a time t3 preferably equal to 60 minutes, in order to speed up the evaporation of the solvent and the adhesion between the lower face and the CaF2 slide.

According to another embodiment, another effective method of gluing is the use of a biocompatible double-sided tape. This eliminates the risk of any polymer pouring into the microchannels and their consequent occlusion. For gluing with double-sided tape, it's necessary to firstly cut out the desired shape of adhesive, then to place the CaF2 slide on it and to apply localized pressure with weights during a treatment in the oven at 70° for about 60 minutes. The criticalities of this procedure are represented by the possible breakage of the slide due to the excessive weight applied during the gluing phase or, alternatively, to the presence of a non-planar support surface that generates localized stresses on the slide, causing it to break.

The device can be coupled to Raman microscopy instruments and chemical and biochemical information is obtained without any pretreatment of the sample. The advantage is that the analyzed sample is not destroyed. Compatibility with Raman microscopy is due to the choice of materials and the passive operation of the device, i.e. no particular set up is required and can be easily coupled to spectroscopy instruments. Another advantage is that it has microfluidic protocols, i.e. the device has multiple chambers and allows to check even complex samples.

Advantageously, the microfluidic device according to the invention allows the creation of dynamic environments.

Advantageously, according to the invention, the microfluidic device has passive and autonomous systems in the management of flows, operating by gravity.

Advantageously, the microfluidic device according to the invention has integrated passively operated valves.

Advantageously, the microfluidic device according to the invention allows easy optical access to the devices, allowing a wide variety of analyzes, through the integrated optical windows.

Advantageously, the microfluidic device according to the invention allows to improve the management of fluid volumes and cells in the various compartments by means of open systems. This configuration in fact facilitates injection and sampling.

Advantageously according to the invention, the microfluidic device uses low cost materials and technologies so that each chip is economical.

Advantageously, according to the invention, the microfluidic device integrates sensors such as to provide detailed biochemical, metabolic, morphological information, including plasmonic technologies.

Finally, it is clear that modifications and variations may be made to the microfluidic device for cell cultures and screening described and illustrated here without departing from the protective scope of the present invention, as defined in the attached claims.

The invention claimed is:

1. A microfluidic device for cell culture and screening, comprising:

a covering element, comprising a plurality of openings, and a through hole having diameter and located in an external face of the coving element;

an intermediate element, comprising on a lower surface of the intermediate element below the covering element a plurality of microchannels, a plurality of supply tanks, at least one waste tank, and at least one culture chamber comprising a central through hole having a diameter, and on an upper surface of the intermediate element below the covering element a blind bottom cavity having a diameter equal to the diameter of the central through hole;

a lower element, comprising on an upper surface of the lower element below the intermediate element a collecting tank and a central through hole having a diameter, and on a lower surface of the lower element below the intermediate element a recessed central portion having a diameter equal to the diameter of the through hole and the blind bottom cavity and a housing pocket; and a slide housed in the housing pocket obtained in the recessed central portion of the lower element;

wherein said intermediate element is assembled and interposed as a layer between the covering element and the lower element to form an upper optical window in a central position, the central through hole obtained in the intermediate element and the central through hole obtained in the lower element being closed at a bottom by the slide, and the plurality of supply tanks and the at least one waste tank are connected to each other by the plurality of microchannels, wherein the plurality of supply tanks comprises a first tank, a second tank, a third tank and a fourth tank, and wherein the plurality of openings is configured to introduce fluids inside the plurality of supply tanks and the at least one waste tank.

2. The microfluidic device according to claim 1, further comprising a plurality of valves configured to manage flow of the fluids in the plurality of microchannels.

3. The microfluidic device according to claim 1, wherein said covering element has a thickness comprised between 5 mm and 1 mm, said intermediate element has a thickness comprised between 4 mm and 8 mm and said lower element has a thickness comprised between 5 mm and 1 mm.

4. The microfluidic device according to claim 1, wherein said covering element, said intermediate element and said lower element each respectively comprise at least four alignment holes each located at respective corner ends of each of the covering element, intermediate element, and lower element, wherein the at least four alignment holes are configured for assembling the microfluidic device.

5. The microfluidic device according to claim 1, wherein the covering element, the intermediate element and the lower element are made of polymethylmethacrylate (PMMA).

6. The microfluidic device according to claim 1, wherein the plurality of microchannels include microchannels each having a rectangular section having a width between 0.005 mm and 0.5 mm and a height between 0.005 mm and 0.5 mm.

7. The microfluidic device according to claim 1, wherein each of the plurality of microchannels is incoming or outgoing from the at least one culture chamber and is placed at a height between 0.005 mm and 0.5 mm from a bottom of said at least one culture chamber.

8. The microfluidic device according to claim 1, further comprising a discharge microchannel that starts from the at least one culture chamber, said discharge microchannel departing and flowing into the waste tank through a recess made on the upper surface of the lower element.

9. The microfluidic device according to claim 1, wherein the slide is made of an optically transparent, comprising CaF2, or of quartz, or other types of glass such as borosilicates, aluminosilicates, soda lime, or of some types of polymers.

10. A production method of the microfluidic device according to claim 1, the method comprising:

making the covering element, the intermediate element and the lower element through micro-milling;

cleaning the covering element, the intermediate element and the lower element by ultrasonic cavitation in a bath of distilled water;

assembling the covering element, the intermediate element and the lower element together by solvent-assisted bonding;

making the optical windows and the housing pocket able to house the slide through micro-milling; and fixing the slide in the housing pocket able to house the lower element.

11. The production method according to claim 10, wherein the step of assembling the covering element, the intermediate element and the lower element by solvent-assisted bonding further comprises:

immersing into a container including ethanol the covering element, the intermediate element and the lower element;

covering the container with aluminum foil to avoid ethanol evaporation;

after a time interval of 80 minutes has passed, assembling the covering element, the intermediate element and the lower element, and fixing the assembled covering element, the intermediate element and the lower element with screws placed in the alignment holes, and placing the fixed elements in a pre-heated pneumatic press for a time interval of 70 minutes.

* * * * *